United States Patent [19]
Mohan et al.

[11] Patent Number: 5,851,907
[45] Date of Patent: Dec. 22, 1998

[54] METHOD FOR REMOVAL OF BINDING PROTEINS FROM LIGANDS

[76] Inventors: Subburaman Mohan, 1414 Diamond Ct., Redlands, Calif. 92374; David J. Baylink, 1428 Serpentine, Redlands, Calif. 92373

[21] Appl. No.: 606,234

[22] Filed: Feb. 23, 1996

Related U.S. Application Data

[63] Continuation of Ser. No. 171,069, Dec. 20, 1993, abandoned.
[51] Int. Cl.$^6$ .................................................. G01N 33/543
[52] U.S. Cl. ......................... 436/518; 435/7.9; 435/7.92; 435/7.93; 435/7.94; 530/412; 530/417
[58] Field of Search .......................... 435/7.9, 7.92–7.94; 530/412, 417; 436/518

[56] References Cited

U.S. PATENT DOCUMENTS 5,198,340  3/1993  Mukku ..................................... 435/7.8

OTHER PUBLICATIONS

Buus et al., "Receptor–Ligand Interactions Measured by an Improved Spun Column Chromatography Technique . . . " Biochim. et Biophys. Acta, 1243:453–460, 1995.
Zapf et al., "Radioimmunological Determination of Insulin–like Growth Factors I and II in Normal Subjects and in Patients with Growth Disorders and Extrapancreatic Tumor Hypoglycemia," *J. Clin. Invest.,* 68:1321–1330, 1981.
Daughaday "[24] Radioligand Assays for Insulin–like Growth Factor II, "Methods in Enzymology, 146:248–259, 1987.
Biorad Life Science Research Products Catalog pp. 17, 18, 19, 20, 1991.
Miller, Jr. et al., "A Miniature Molecular Sieving Column Assay for Cytoplasmic Vitamin A–Binding Proteins," Anal. Biochem. 139:104–114, 1984.
BioRad Life Science Research Products–Price List S. pp. 16–18, 1993.
Flynn et al., "Peptide Binding and Release by Proteins Implicated as Catalysts of Protein Assembly," Science 245: 385–390, 1989.
Pretzman et al., "Rapid Separation of IgM from Whole Serum Using Spun Column Chromatography," J. of Immunol. Methods 83:30–307, 1985.

Chen et al., "Identification of a Soluble Salicylic Acid–Binding Protein That May Function in Signal Transduction . . . " PNAS 88:8179–8183, 1991.
Bio–Rad Catalog. Mar. 1991. pp. 17–21.
Deutscher, M.P., ed. Guide to Protein Purification. *Methods in Enzymology* 182:317–328,1990.
Neal M.W. et al. "A rapid method for desalting small volume of solution." *Analytical Biochemistry* 55:328–330, 1973.
Rawn, D.J. Biochemistry. New York: Harper and Row, 1980, p. 183.
Sambrook, J. et al. Molecular Cloning: A Laboratory Manual. Cold Spring Harbor, New York: Cold Spring Harbor Laboratory Press, 1989. pp. E37–E38.
Daughaday et al., "Inhibition of Access of Bound Somatomedin to Membrane Receptor and Immunobinding Sites: A Comparison of Radioreceptor and Radioimmunoassay of Somatomedin in Native and Acid–Ethanol–Extracted Serum," *J. Clin. Endocrinol Metab.,* 51:781–788, (1980).
Daughaday et al., "Insulin–Like Growth Factors I and II. Peptide, Messenger Ribonucleic Acid and Gene Structures, Serum, and Tissue Concentrations," *Endocrine Rev.,* 10:68–91, (1989).
Shimasaki & Ling, *Progress in Growth Factor Research,* 3:243–266 (1991).
Mohan and Baylink, "Evidence that the Inhibition of TE85 Human Bone Cell Proliferation by Agents which Stimulate cAMP production may in part be Mediated by Changes in the IGF–II Regulatory System," *Growth Regulation* 1:110–118 (1991).
Breier et al., "Radioimmunoassay for insulin–like growth factor–I: solutions to some potential problems and pitfalls," *J. Endocrinol.,* 128:347–357 (1991).
Lehninger, A.L., Principles of Biochemistry. New York: Worth Publishers, 1982., pp. 81–89.
Pharmacia, Affinity Chromatography Principles & Methods, printed 1986–8, pp. 49–51.

*Primary Examiner*—Carol A. Spiegel
*Attorney, Agent, or Firm*—Popovich & Wiles, P.A.

[57] ABSTRACT

The present invention provides methods for separating ligands from binding proteins. The methods include acidic separation and size separation. The methods of the present invention are particularly useful for separating insulin-like growth factors from insulin-like growth factor binding proteins.

23 Claims, 9 Drawing Sheets

METHOD FOR REMOVAL OF BINDING PROTEINS FROM LIGANDS

This is a continuation of application Ser. No. 08/171,069, filed Dec. 20, 1993, now abandoned.

BACKGROUND OF THE INVENTION

The present invention relates generally to methods for separating binding proteins from ligands. More particularly, the present invention provides separation methods incorporating acidic extraction and size separation. The methods of the present invention are useful for separating a variety of proteins, especially separating insulin-like growth factors from insulin-like growth factor binding proteins.

Separation of binding proteins from ligands is important in a variety of clinical diagnostic settings. For example, the dissociation of insulin-like growth factors (IGFs) from insulin-like growth factor binding proteins (IGFBPs) is essential for performance of valid IGF radioligand assays. The IGFBPs must also be removed from the sample to be assayed. Otherwise, the presence of IGFBPs in the sample may result in significant artifacts in the radioligand assays.

IGF-I and IGF-II, previously known as somatomedins, are structurally related to insulin and are the two most abundant polypeptide growth factors that circulate in human plasma (Daughaday et al., *Endocrine Rev.*, 10:68–91, 1989). IGF-I and IGF-II participate in regulation of cellular proliferation in many cell types including cells derived from brain, thyroid, liver, muscle, kidney, blood and bone. Many of these cell types have been shown to produce IGFs in culture, contain high affinity receptors for IGFS, and exhibit biological responses to exogenously added IGFs. Thus, IGFs apparently play a significant role in local regulation of cellular proliferation. IGFs produced by one cell type can act on the same cell type in an autocrine manner or on neighboring cell types in a paracrine manner.

IGFs circulate in plasma as large molecular weight proteins bound to specific proteins which are termed IGF binding proteins (IGFBPs). Six different IGFBPs (designated IGFBP-1 through IGFBP-6) have been purified and cloned from a variety of human tissues (Shimasaki & Ling, *Progress in Growth Facor Research*, 3:241–266 (1991)). IGFBPs have several important functions, including, e.g., 1) prevention of the acute metabolic effects of free IGFs, specifically hypoglycemia, 2) increasing the half life of the IGFs in the circulation, 3) regulation of the bioavailability of IGFs in local areas and 4) provision of tissue specificity for the local action of IGFs.

The existence of these IGFBPs in serum and in other biological fluids, such as conditioned medium, has complicated the application of specific radioligand assays (radioimmunoassay and radioreceptor assay) for measurement of IGFs. Naturally occurring IGFBPs in the sample can compete with the antibody or receptors for tracer binding, thus reducing the amount of tracer available for binding with the capture antibody or receptor. This competitive binding causes a reduction of radioactive signal bound to the antibody or receptor. The reduction in tracer binding is generally interpreted as a falsely elevated amount of immunoreactive IGF in the sample.

IGF measurements made using methods in which IGFBP artifacts are not removed may produce erroneous results because of the interaction of IGFBPs and tracer molecules. For example, forskolin and dibutyryl cyclic AMP treatment increase IGF-I like and IGF-II like activity in the conditioned medium of TE85 human osteosarcoma cells. The observed apparent increase in radioligand activity was due to increased production of IGFBP-4 and not due to IGFs (Mohan and Baylink, Growth Regulation 1:110–118 (1991)). Thus for valid measurements of IGFS, the dissociation of IGFs from IGFBPs and elimination of IGFBPs from the sample must precede the measurement of IGFs in the radioligand assays.

As measurements of IGFs are useful in assessing many clinical disorders, including several growth related disorders, tumor induced hypoglycemia, and nutritional status, an extraction method which eliminates interference associated with IGFBPs is essential. Increasing interest in elucidating the physiological role of IGFs and extensive use of IGF radioligand assays for clinical diagnosis has led to the application of some incompletely characterized or validated assays for measurement of IGFs in biological fluids. A number of strategies have been used to eliminate IGFBPs in human serum samples including acid gel filtration, acid ethanol extraction and C-18 SEP-PAK separation (Zapf et al., *J. Clin. Invest.*, 68:1321 (1981); Daughaday et al., *J. Clin. Endocrinol Metab.*, 51:781 (1980); Daughaday, *Methods in Enzymology*, 146:248 (1987)). Of these procedures, acid ethanol extraction has been the most widely used because of its simplicity.

Because of the presence of multiple IGFBPs in biological fluids which produce serious artifacts in IGF radioligand assays and because IGFBPs and IGFs could be regulated independently of each other, it is essential to remove all the IGFBPs in order for the results to be valid. Although acid ethanol extraction and SEP-PAK separation have been used extensively in the literature for removing IGFBP artifacts in the biological samples, these two methods are not reliable because IGFBP artifacts are often incompletely removed. Compounding the problem, the relative level of interference in acid ethanol extracted and SEP-PAK extracted serum samples may vary between laboratories. Several variables influence the degree of interference including 1) the relative affinities of the capture antibody and the IGFBP to the tracer, 2) the concentration of capture antibody used in the assay and the concentration of IGFBP remaining in the sample, and 3) the relative concentration of IGFs and IGFBPs in the extracted samples. As the amount of antibody used in IGF radioligand assays is usually limited, the IGFBPs must be considered an important variable that may produce artifacts in acid gel filtration and SEP-PAK separation.

Other methods, such as SEPHADEX G-75 separation, are labor intensive and require many hours for completion. While these methods are generally more reliable than acid ethanol SEP-PAK extraction, neither is suitable for rapidly processing many samples as is required by clinical laboratories.

A variety of other ligands are associated with binding proteins in the body. These include, e.g., thyroid hormone that is naturally bound to thyroglobulin, many drugs that bind serum proteins (primarily albumin), testosterone, growth hormone, transforming growth factor beta, fibroblast growth factor, bone morphogenetic proteins, and the like. Separation of these ligands from their associated binding proteins is important for accurate clinical assessment. As described for insulin-like growth factors above, methods for separating these ligands and binding proteins should be relatively easy to perform and produce reliable results.

What is needed in the art are methods of separating ligands and binding proteins in biological samples in a manner that reliably separates the ligand for assays. Preferably, the method will be rapid, relatively inexpensive, and easily reproducible. Quite surprisingly, the present invention fulfills these and other related needs.

SUMMARY OF THE INVENTION

The present invention provides novel methods for separating ligands from binding proteins in a sample. Generally, the methods include applying the sample to an acidic gel centrifugation column; centrifuging the column to elute fractions of the sample; and collecting the eluted fractions. The methods are particularly useful for separating insulin-like growth factors from insulin-like growth factor binding proteins. The methods combine size exclusion with acidic separation. Generally, the samples will be blood, plasma, serum, urine, or conditioned media.

The present invention also provides methods for determining the concentration of an insulin-like growth factor in a sample. The methods generally comprise applying the sample to an acidic gel centrifugation column; centrifuging the column to elute fractions of the sample; collecting the eluted fractions; quantifying the amount of insulin-like growth factor in the sample; and determining therefrom the concentration of insulin-like growth factor in the sample. The amount of insulin-like growth factor in the sample may be quantified by several methods, including, e.g., immunoassays and insulin-like growth factor receptor binding assays. Free (unbound) insulin-like growth factor concentrations may also be determined in a sample by elution of sample fractions from the column with neutral buffers. The ratio of the free to total concentrations of insulin-like growth factor may be calculated from the above methods.

DETAILED DESCRIPTION OF SPECIFIC EMBODIMENTS

Figure 1A:
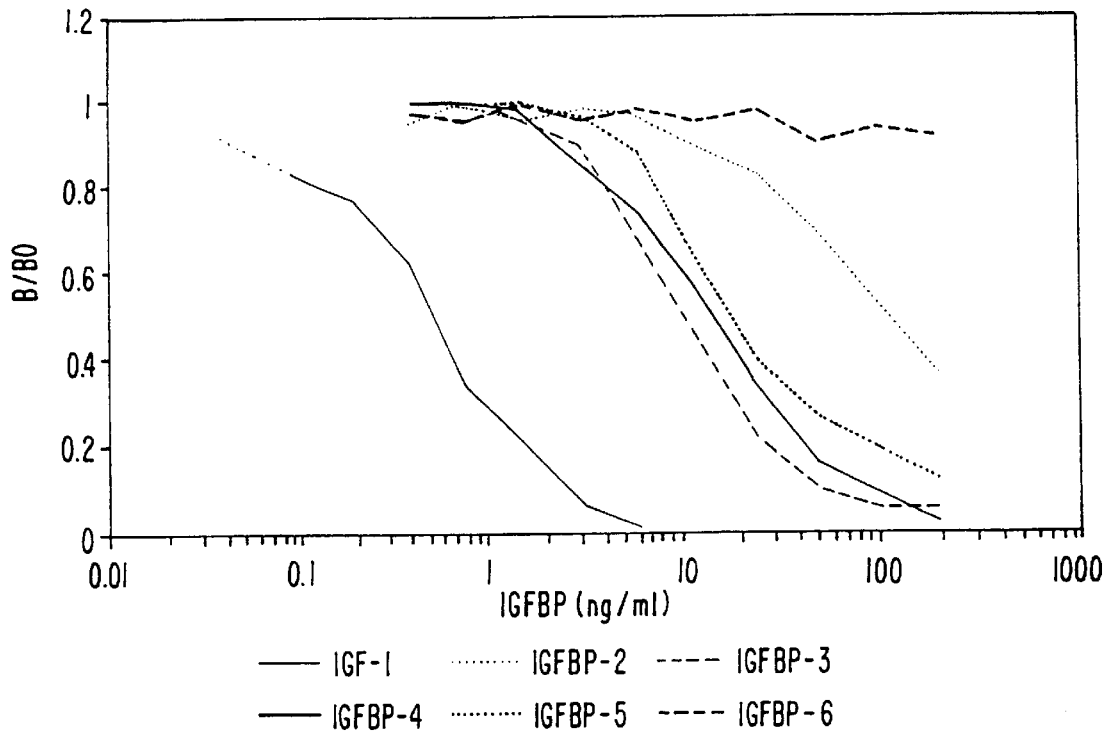
FIG. 1A illustrates IGFBP interference of competitive binding between labelled and unlabelled IGF-I.

The present invention provides novel methods for separating ligands from binding proteins. The methods are particularly useful for separating insulin-like growth factors from insulin-like growth factor binding proteins. The methods provide a rapid, reproducible means for separation, thus allowing accurate and reproducible clinical measurement of insulin-like growth factor in clinical samples.

The methods generally include a combination of acidic separation and size separation. The methods may be employed to separate a wide variety of ligands from binding proteins. The bound ligands may include hormones, drugs, and the like. The ligand and binding protein dissociate under the acidic conditions and are subsequently separated by size. Dissociation occurs below the pKa of the binding pair. By "binding pair," it is meant the subject ligand and its associated binding protein. The separation pH will generally be chosen to be slightly more acidic than the pKa (generally a pH that is at least 0.01–0.05 less than the pKa of the binding pair, although this may vary with different ligands and binding proteins). This will maximize the probability that the binding pair may be separated while avoiding denaturation of the ligand. It is generally preferred to avoid denaturation of the ligand as the ligand is often detected and quantified in binding assays. Denaturation of the ligand may result in alteration of the binding region so as to inhibit binding in the detection assay, thereby producing false results. When the pKa of the binding pair is close to the denaturation pH of the ligand, the pH of the ligand-containing fraction may be normalized following size separation prior to further detection or quantification.

Methods for separating ligands from binding proteins in a sample are provided by the present invention. The methods generally comprise applying the sample to an acidic gel centrifugation column and centrifuging the fractions to elute fractions of the sample. By "acidic gel centrifugation," it is meant a gel chromatography column suitable for centrifugation separations in which the gel has an acidic pH. As used herein, "fractions of the sample" is meant to indicate solutions obtained from passage of constituents of the sample through the centrifugation column. The fractions may be comprised solely of constituents of the sample or may contain constituents of the sample and an elution buffer.

Typically, the methods are applied to separation of insulin-like growth factors from insulin-like growth factor binding proteins. The method may be used to separate either insulin-like growth factor-I or insulin-like growth factor-II from any of the insulin-like growth factor binding proteins (e.g., IGFBPs 1–6). Methods of the present invention for separating insulin-like growth factors from insulin-like growth factor binding proteins in a sample generally include applying the sample to an acidic gel centrifugation column, centrifuging the column to elute fractions of the sample, and collecting the eluted fractions.

The methods of the present invention may be applied to a variety of samples. Generally, the samples will be a fluid obtained from a patient, such as, e.g., blood, serum, plasma, urine, cerebrospinal fluid, ascites, or interstitial fluids. Samples from patients may be processed prior to undergoing separation by the methods of the present invention, e.g., removing cells from whole blood. Solid tissue may also be processed to provide samples for use with the claimed methods. The solid tissue is generally minced and may be mechanically or enzymatically homogenized in appropriate extraction buffer. The homogenized tissue may then be mixed with an appropriate diluent and subjected to the separation methods of the present invention. Alternatively, the sample may be a laboratory sample, such as conditioned media from cell culture. Conditioned media samples may be assayed directly or prepared by methods well known in the art. Persons of skill will appreciate the proper conditioned media preparation methods to apply to different types of samples.

The sample is applied to an acidic gel centrifugation column. Generally, particulate matter, such as cells or cellular debris, will be removed from the sample prior to application to the column. Otherwise, the particulate matter may interfere with size separation by blocking the pores of the column. In some instances, the sample may be diluted with a physiological carrier, such as, e.g., saline or fetal calf serum, to provide a less viscous sample that will flow through the column more readily.

Typically, a polyacrylamide gel centrifugation column will be employed. The gel must be resistant to degradation in acidic conditions. Generally, the gel will be resistant to conditions as acidic as pH 2 or lower, although this may vary with the nature of the ligands and binding proteins to be separated. The acid resistance of the gel may be determined by the pKa of the binding pair to be separated. Gels useful for the separation of insulin-like growth factor from insulin-like growth factor binding protein will generally be resistant to acidic conditions of pH 2.

Also, the gel will generally be resistant to significant deformation under pressure. The gel should generally withstand pressures as high as 12–20 pounds per square inch or higher. Higher centrifugation velocities will generally be required for size separation of binding pairs in which the ligand and the binding protein are of similar size. In these instances, the gels should withstand higher pressures associated with higher centrifugation velocities. Otherwise, the gel may form an impenetrable mass or lose its inherent pore structure that provides for size separation.

The exclusion limit of the gel will be determined by the size of the ligand and binding proteins to be separated. Generally when separating insulin-like growth factors from insulin-like growth factor binding proteins, the exclusion limit will be about 20,000 daltons. This allows larger insulin-like growth factor binding proteins to be eluted in the void volume while retaining the smaller insulin-like growth factors. Persons of skill will readily appreciate how to select the appropriate exclusion limit for the ligands and binding proteins to be separated based upon their relative size.

Suitable gels are commercially available from a variety of sources. One particularly useful gel for separation of insulin-like growth factors from insulin-like growth factor binding proteins is BIO-GEL P-10 from BioRad Laboratories, Hercules, Calif. BIO-GEL P-10 is resistant to pH 2 conditions, will not significantly deform under pressures of 15 pounds per square inch, and has an exclusion limit of 20,000 daltons. Gel preparations are available from other manufacturers, e.g., SEPHADEX G50, Pharmacia Fine Chemicals, Uppsala, Sweden; however these gels may not be capable of withstanding the centrifugal force employed in the methods of the present invention.

The gels may be obtained in gelatinous form or hydrated from a powder. When hydrated from a powder, it will often be desirable to hydrate the gel with an acid, such as, e.g., 1M acetic acid. Pre-hydrated gels may also be soaked in an acidic solution, e.g., 1M acetic acid, prior to use in the methods of the claimed invention. Following hydration or soaking in an acidic solution, the gels may be pretreated with bovine serum albumin or other serum proteins, such as gamma globulin. Pretreatment will often increase the yield of insulin-like growth factors by limiting the retention of the insulin-like growth factors in the gel. Typically, pretreatment will not affect the efficiency of separation of the components of the sample. Generally during pretreatment, the gels are incubated with the pretreatment agent overnight.

The gel centrifugation columns may be obtained commercially, e.g., BIO-SPIN columns from Bio-Rad, Hercules, Calif. Alternatively, the gel centrifugation columns may be constructed by common methods well known to those of skill in the art, such as described in Sambrook et al., *Molecular Cloning, A Laboratory Manual,* Cold Spring Harbor Press, 1989, incorporated herein by reference. Briefly, the bottom of a 1 ml disposable syringe is plugged with sterile glass wool. Hydrated gel is added to the syringe in a buffer solution by gently tapping the sides of the syringe until filled. The syringe is centrifuged at 1600×g for 4 minutes. Gel is added to the syringe and centrifuged again. This is repeated until the packed volume is about 0.9–1.1 ml. The column is then ready for pretreatment as described above.

Following complete preparation of the column, the sample is mixed with an acidic solution, such as, e.g., acetic acid or HCl. For separation of insulin-like growth factor from insulin-like growth factor binding proteins, the pH of the resulting sample solution will generally be about 1 to about 3, usually about 2. The solution is added to the column. The column is centrifuged at about 500 to 2000×g, usually about 1250×g for 2–10 minutes. Fractions are eluted from the column during centrifugation. When separating insulin-like growth factor binding proteins from insulin-like growth factors, the void volumes will generally contain all of the binding proteins.

Following collection of the void volume, elution buffer is added to the column. Additional fractions are eluted from the column by sequentially loading the column with elution buffer and centrifuging the loaded column. The elution buffer should generally be approximately the same pH as the sample solution to prevent re-association of the binding pair. When separating insulin-like growth factor binding proteins from insulin-like growth factors, a convenient buffer is 1M acetic acid in 0.1M NaCl. Using this elution buffer, the insulin-like growth factors are generally eluted in the fourth and fifth fractions.

Fractions containing insulin-like growth factors and insulin-like growth factor binding proteins may be identified by several methods well known to those of skill in the art. For example, a known amount of labeled insulin-like growth factor may be added to the sample. Fractions containing insulin-like growth factor will contain the labeled insulin-like growth factor. Therefore, detection of fractions containing the label will identify the insulin-like growth factor-containing fractions. Insulin-like growth factor binding protein-containing fractions may be identified in a similar fashion.

Fractions containing other ligands and binding proteins may be identified as explained above. Labelled ligand or binding protein may be added to the sample and identified in the eluted fractions. The sample ligand and/or binding proteins may be identified and quantitated as described below.

The present invention also provides methods for determining the concentration of insulin-like growth factor in a sample. The methods generally include applying the sample to an acidic gel centrifugation column, centrifuging the column to elute fractions of the sample, collecting the eluted fractions, quantifying the amount of insulin-like growth factor in the fractions, and determining therefrom the concentration of insulin-like growth factor in the sample.

These methods separate insulin-like growth factors from insulin-like growth factor binding proteins in the sample by centrifuging the sample in an acidic gel centrifugation column. The fractions containing insulin-like growth factor may be identified as described above. The quantity of insulin-like growth factor in the fractions may be quantified by methods well known to those of skill in the art.

One convenient method of quantitating insulin-like growth factors in samples is by immunoassay. A wide variety of immunoassays may be employed as generally described in Harlowe and Lane, *Antibodies, A Laboratory Manual*, Cold Spring Harbor, 1988, incorporated herein by reference. The immunoassays may be direct or indirect. Monoclonal and polyclonal antibodies may be raised against insulin-like growth factors by methods well known to those of skill in the art. Alternatively, antibodies that react with insulin-like growth factors may be obtained commercially from suppliers such as the National Hormone and Pituitary Program, Baltimore Md. or Amano Pharmaceuticals, Troy, Va. In direct immunoassays, the antibodies may be labeled. Suitable labels include enzymes, such as alkaline phosphatase and horseradish peroxidase, radioactive labels, such as $^{125}I$, chromophores, such as Texas red, and fluorochromes, such as fluorescein isothiocyanate.

Generally, the assays will be competitive binding assays. Antibodies that react with insulin-like growth factor are immobilized on a support. Elution fractions containing insulin-like growth factor are mixed with labelled insulin-like growth factor. The mixture is applied to the immobilized antibodies. Insulin-like growth factors, both from the sample as well as the added labelled molecules, will competitively bind the immobilized antibodies and be retained. Measurement of the retained label will provide an indirect measurement of the concentration of insulin-like growth factor in the sample. Alternative methods of immunoassay may also be employed, such as antibody sandwich assays.

Another method for quantifying the amount of insulin-like growth factor in a sample is by receptor assays. For example, IGF receptors may be bound to a solid support. IGF-containing fractions may be contacted with the immobilized receptors. IGF in the assayed fraction will bind to the receptors and other constituents of the fraction may be washed from the solid support. Labelled antibodies specific for IGF may be contacted with the solid support either simultaneously with or following exposure of the solid support to the assayed fraction. The antibodies will bind to IGF which in turn binds to, and is retained by, the immobilized IGF receptors. This results in retention of the label on the solid support following washing in direct proportion to the amount of IGF in the assayed fraction. Therefore, the amount of IGF in the fraction may be determined from measurement of retained label.

Detection and quantification of other ligands may be similarly performed. For example, either immunoassays or receptor-based assays may be employed to detect and quantify ligands as described above. Antibodies and/or receptors specific for ligands to be detected may be employed in these assays.

Free ligands in a sample may also be quantified by the methods of the present invention. Generally, the sample is applied to a neutral gel centrifugation column. By "neutral gel centrifugation column," it is meant a gel chromatography column suitable for centrifugation in which the gel has a neutral pH, generally from about pH 6.5 to about pH 7.5, more preferably about pH 7. The column is centrifuged and the fractions collected. Neutral buffers are used to collect fractions following elution of the void volume. Ligands bound to binding proteins are generally eluted before free ligand. Fractions containing free ligand may be identified by adding labelled free ligand to the sample and detecting the presence of the label in the fractions. Free ligand may then be quantified in the appropriate fractions as described above.

Free IGFs in a sample may be detected as follows. Fifty $\mu l$ of sample is diluted with about 200 $\mu l$ of a neutral buffer, such as 0.05M sodium phosphate buffer (pH 7.5) containing 0.6% sodium chloride, 0.1% sodium azide, and 0.05% TWEEN 20. BIO-GEL P-10 is equilibrated in the buffer and a centrifugation column prepared as described above. The column is centrifuged to remove the buffer. Fifty $\mu l$ of the diluted sample is applied to the column and centrifuged at about 1250×g for 3–5 minutes. Neutral buffer is applied and the column is centrifuged an additional two times. The bound IGFs are eluted in these initial three fractions. One ml of the neutral buffer is applied to the column which is centrifuged for 5 minutes at about 1250×g. The free IGFs are eluted in this fraction. The free IGF pool is collected in a polypropylene tube and used for IGF assays as described above. The concentration of free IGFs in the sample may be determined following quantification of the free IGFs in the final fraction.

The ratio of the concentrations of free to total ligands may be determined by the methods of the present invention. A sample is divided into equal aliquots. One aliquot is diluted in an acidic buffer having the appropriate pH. Another aliquot is diluted in a neutral buffer. The concentrations of free ligand and total ligand are determined as described above. The ratio of the concentrations may then be calculated.

The following examples are offered by way of illustration and not limitation.

EXAMPLES

Example I

Assessment of Interference of IGFBPs in IGF Radioligand Assays

Figure 1B:
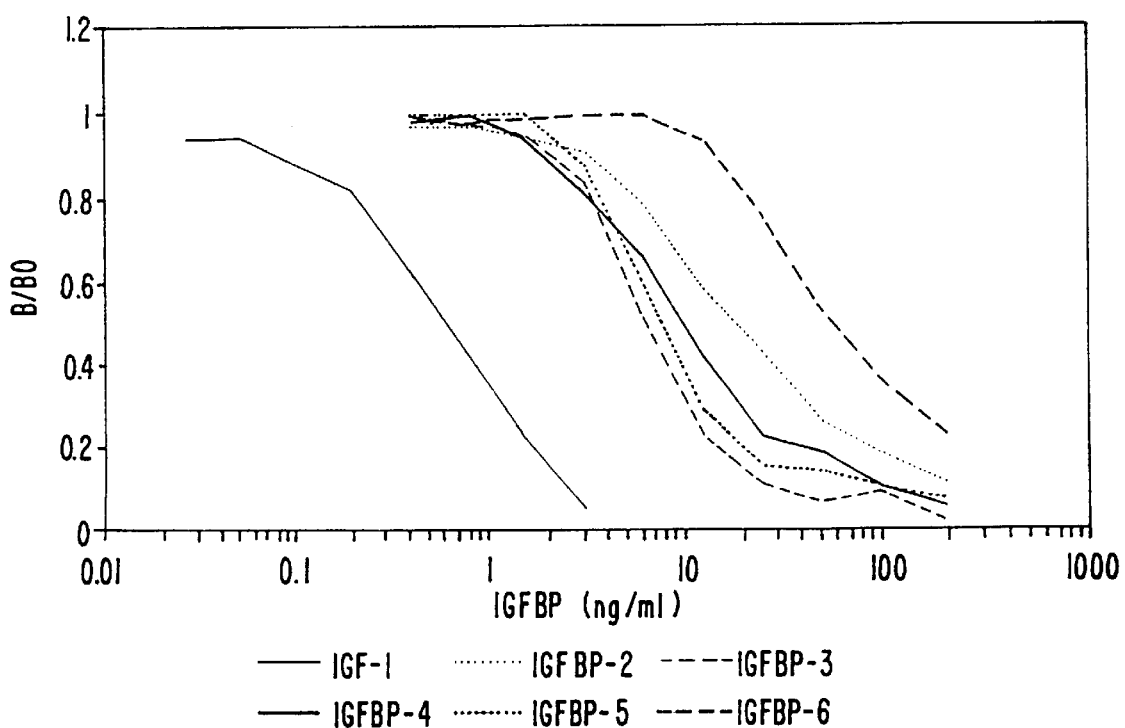
FIG. 1B illustrates IGFBP interference of competitive binding between labelled and unlabelled IGF-II.

Competition for $^{125}I$-IGF binding to antibody was determined in the presence and absence of different concentrations of purified IGFBPs to determine the extent of interference by different IGFBPs in IGF radioligand assays. All IGFBPs assayed (IGFBP-2–IGFBP-6) substantially inhibited binding of IGF-II (FIG. 1B). All IGFBPs except IGFBP-6 substantially inhibited IGF-I binding (FIG. 1A).

The following IGF radioligand assay was employed for all assays. Standards and unknowns (0.1 ml) were added to polypropylene tubes containing 0.2 ml RIA buffer (0.04M sodium phosphate buffer, pH 7.2 supplemented with 0.5% BSA and 0.02% sodium azide) and pre-incubated for 1 hour at room temperature with 0.1 ml primary antibody (1:6000 dilution of rabbit polyclonal antiserum produced against IGF-I (National Hormone and Pituitary Program, Baltimore, Md.); or 1:6400 dilution of 10 μg/ml IGF-II monoclonal antibody (Amano Pharmaceuticals, Troy, Va)). 0.1 ml of $^{125}$I-IGF tracer (30,000–40,000 cpm) was added to the mixture and the tubes were incubated for an additional 16 hours at 4° C.

Bound $^{125}$I-IGF was separated from free $^{125}$I-IGF by adding 0.1 ml of a 1:20 dilution of appropriate nonimmune serum, 0.4 ml of appropriate dilution of goat antirabbit or goat antimouse immunoglobulin G, and 0.2 ml of 8% polyethylene glycol 8000. The samples were mixed and incubated at room temperature for 2 hours. The precipitates were pelleted by centrifugation, and counted in a gamma counter. The percentage of $^{125}$I-IGF tracer bound in the presence and absence of IGFBP was plotted against the concentrations of each IGFBP used in the study.

All purified IGFBPs except IGFBP-6 decreased the binding of $^{125}$I-IGF-I to antibody in a dose dependent manner. Fifty percent inhibition of $^{125}$I-IGF-I by each IGFBP except IGFBP-6 was observed between 10 and 100 ng/ml. Purified IGFBP-3, IGFBP-4 and IGFBP-5 were several fold more potent than the other IGFBPs for inhibiting binding of $^{125}$I-IGF-I tracer to antibody. The interference of IGFBPs was much more evident in IGF-II RIA than in IGF-I RIA. Fifty percent inhibition of $^{125}$I-IGF-II binding was observed between 5 and 50 ng/ml for the different IGFBPs. All six IGFBPs decreased the binding of $^{125}$I-IGF-II to antibody in parallel with the IGF-II standard.

All six purified IGFBPs produced artifacts in both IGF-I and IGF-II radioligand assays. The extent of interference varied with the affinity of IGFs to IGFBPs. IGFBP-6 which has the least affinity for IGF-I produced very little artifact in IGF-I RIA. On the contrary, IGFBP-3 and IGFBP-4 which bind IGF-I with the highest affinities produced the greatest artifacts in IGF-I RIA. In addition, IGFBP-2, -5 and -6 which bind IGF-II with higher affinity than IGF-I produced more interference in IGF-II RIA than in IGF-I RIA. These results demonstrate the need to separate IGFs from IGFBPs for insulin-like growth factor assays.

Example II

Efficacy of removal of IGFBPs by SEPHADEX G-75, acid ethanol and SEP-PAK methods The efficacy of IGFBP removal by standard separation and removal methods was determined. Serum samples were extracted by acid ethanol, SEP-PAK, and SEPHADEX G-75 methods. Acid ethanol and SEP-PAK methods did not reliably remove IGFBPs from samples.

Serum was treated with standard acid-ethanol as described by Daughaday et al., *J. Clin. Endocrinol. Metab.*, 51:781 (1980). Briefly, 100 μl of serum was mixed with 900 μl acid-ethanol (12.5% 2M HCl and 87.5% ethanol, v/v). The mixture was incubated at room temperature for 30 minutes. The acid ethanol extract was centrifuged in an Eppendorf microcentrifuge (Brinkman Instruments, Westbury, N.Y.) for 30 minutes at 4° C. In a modified procedure (acid-ethanol cryoprecipitation method), acid-ethanol treated supernatant was neutralized with 0.855M tris base, stored at −20° C. for 1 hour and centrifuged again for 30 minutes in a microcentrifuge as described in Breier et al., *J. Endocrinol.*, 128:347 (1991).

C-18 SEP-PAK columns (Waters Assoc., Medford, Mass.) were used for acid chromatography extraction to separate the IGFs from IGFBPs. Briefly, 50 μl of serum was mixed with 950 μl of 0.5N HCl and incubated for 30 minutes. Two hundred μl of this mixture was applied to a C-18 SEP-PAK column which had been prewet with 5 ml of acetonitrile and then rinsed with 5 ml of water. Unbound proteins were eluted by rinsing the column with 10 ml of 4% acetic acid. Bound proteins (IGFs) were eluted by rinsing the column with 5 ml of 95% acetonitrile containing 0.1% trifluoroacetic acid (TFA). Bound fractions were dried by speed vac centrifugation and used for IGFBP analysis.

FPLC column HR 10/30 (1 cm×30 cm) was packed with SEPHADEX G-75 using 1M acetic acid containing 0.1M NaCl as buffer. 100 μl serum was mixed with 400 μl of 1.25M acetic acid containing 0.125M NaCl and incubated at room temperature for 15 minutes prior to its application to the column using a 200 μl sample loop. The proteins were eluted at a flow rate of 0.5 ml/minute. Two-minute fractions were collected, dried by speed vac centrifugation to remove acetic acid (Savant Instruments, Hicksville, N.Y.), reconstituted in 20 mM acetic acid and used for IGF-I, IGF-II and IGFBP assays. In some experiments, IGFBP (16–30 minutes) and IGF (30–44 minutes) pools were collected in 13×100 mm polypropylene tubes, dried by speed vac centrifugation, reconstituted in 0.5 ml 20 mM acetic acid (1/10 dilution of original sample) and used for IGF assays and for ligand blots.

Untreated, acid ethanol, SEP-PAK and SEPHADEX G-75 extracted serum samples were subjected to acid gel filtration using SEPHADEX G-75 in a FPLC system as described above to separate IGFs from IGFBPs prior to analysis. 0.150 ml of binding assay buffer (0.1M Hepes/44 mM sodium carbonate (pH 6.0)/0.1% TRITON X-100/0.02% sodium azide) and 0.050 ml of $^{125}$I-labeled IGF-I or IGF-II (25,000–30,000 cpm) were mixed in disposable polypropylene tubes and incubated for 1–2 hrs. at room temperature. To separate bound and free $^{125}$I-labeled IGF a combination of bovine gamma globulin and PEG were used. PEG precipitates larger molecules, while the gamma globulin, which is a larger molecule, was added to facilitate the precipitation process. 0.200 ml of 2% bovine gamma globulin in buffer was added to the tubes, mixed, and centrifuged at 1185×g (3,000 rpm) for 20 minutes at room temperature. The supernatants were decanted and the pellets were washed by adding 15% PEG in water to the tubes and re-centrifuging for 20 minutes. The radioactivity in the pellets was counted in the gamma counter. To obtain specific counts, the counts of the control tubes containing buffer and tracer, but not binding protein, were subtracted from the counts of tubes containing both sample and tracer.

Figure 2A:
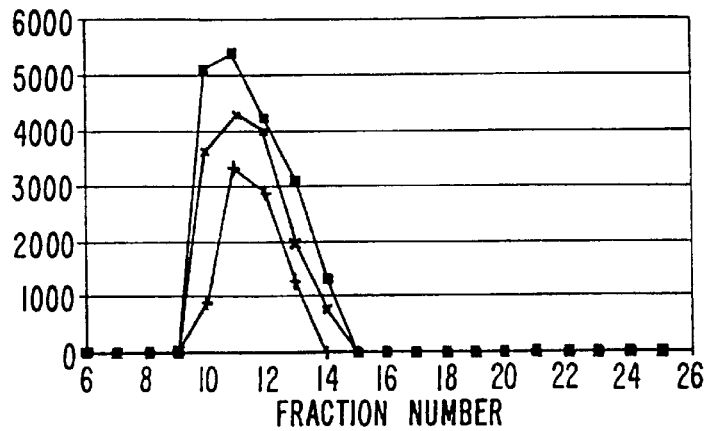
FIG. 2A illustrates the IGFBP elution profile following separation of IGFs from IGFBPs in untreated human serum and serum treated by acid ethanol extraction, C18 SEP-PAK separation, and SEPHADEX G-75.

FIG. 2A shows IGFBP profiles obtained during the acid gel filtration of human serum after various extraction procedures compared with untreated serum sample. IGFBP activity (fractions 9–15) eluted between molecular weight markers BSA (67,000) and myoglobin (17,500). There was no detectable IGFBP activity in the region where IGFs eluted (fractions 15–22). A significant amount of IGFBP activity was retained in the serum samples after extraction with acid ethanol and SEP-PAK, but not after SEPHADEX G-75 acid gel filtration. Although acid-ethanol cryo-precipitation was slightly better than standard acid ethanol extraction, a significant amount of IGFBPs remained unextracted after this procedure.

Figure 2B:
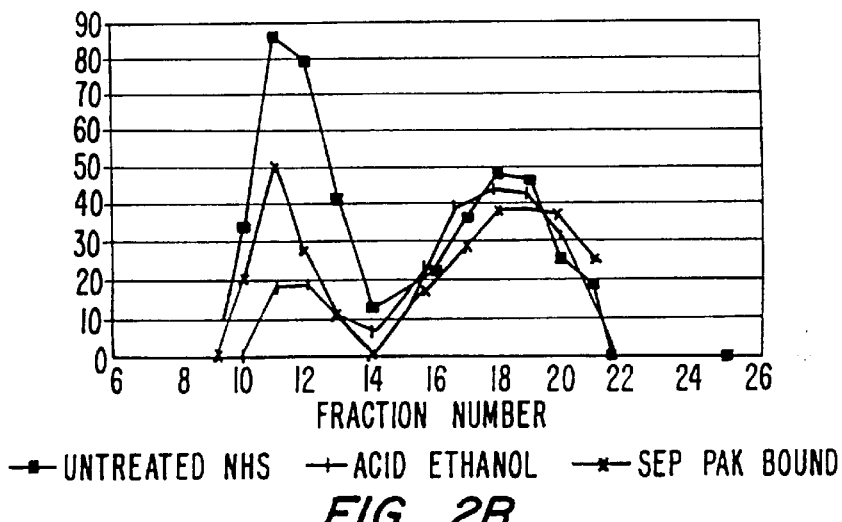
FIG. 2B illustrates the IGF-I elution profile following separation of IGFs from IGFBPs in untreated human serum and serum treated by acid ethanol extraction, C18 SEP-PAK separation, and SEPHADEX G-75.
Figure 2C:
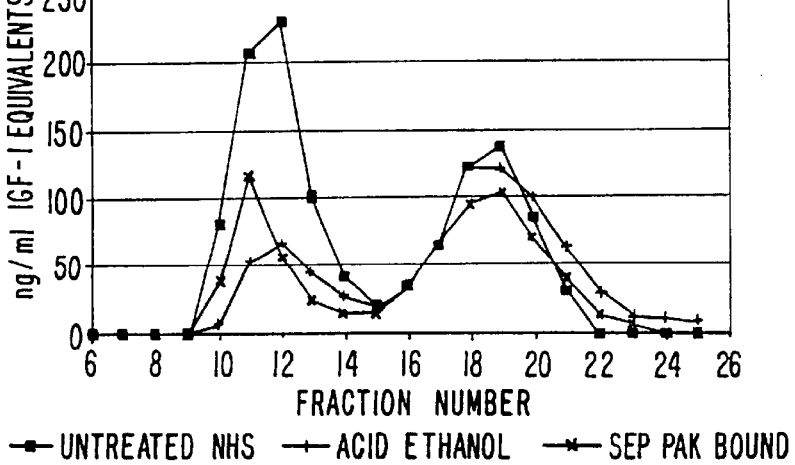
FIG. 2C illustrates the IGF-II elution profile following separation of IGFs from IGFBPs in untreated human serum and serum treated by acid ethanol extraction, C18 SEP-PAK separation, and SEPHADEX G-75.

Analysis of SEPHADEX G-75 fractions for IGF-I and IGF-II activity by RIA yielded two peaks of activity for untreated, acid ethanol and SEP-PAK extracted serum samples (FIGS. 2B and 2C). The high molecular weight IGF-I and IGF-II activity peak (fractions 8–14) corresponded with the IGFBP activity peak suggesting that this peak of IGF-like activity was probably due to IGFBP artifacts. Consistent with this interpretation, preincubation of aliquots of these fractions with excess unlabeled IGF-II or IGF-I (in IGF-I and IGF-II radioligand assays respectively) abolished the IGF-like activity in the IGF RIAs. The low molecular weight IGF activity peak co-eluted with $^{125}$I-IGF and was not abolished upon preincubation with excess of unlabeled IGF. In contrast to acid-ethanol and SEP-PAK extracted serum samples, the IGF pool obtained after SEPHADEX G-75 gel filtration yielded no measurable IGF-like activity in the high molecular weight region.

Figure 3A:
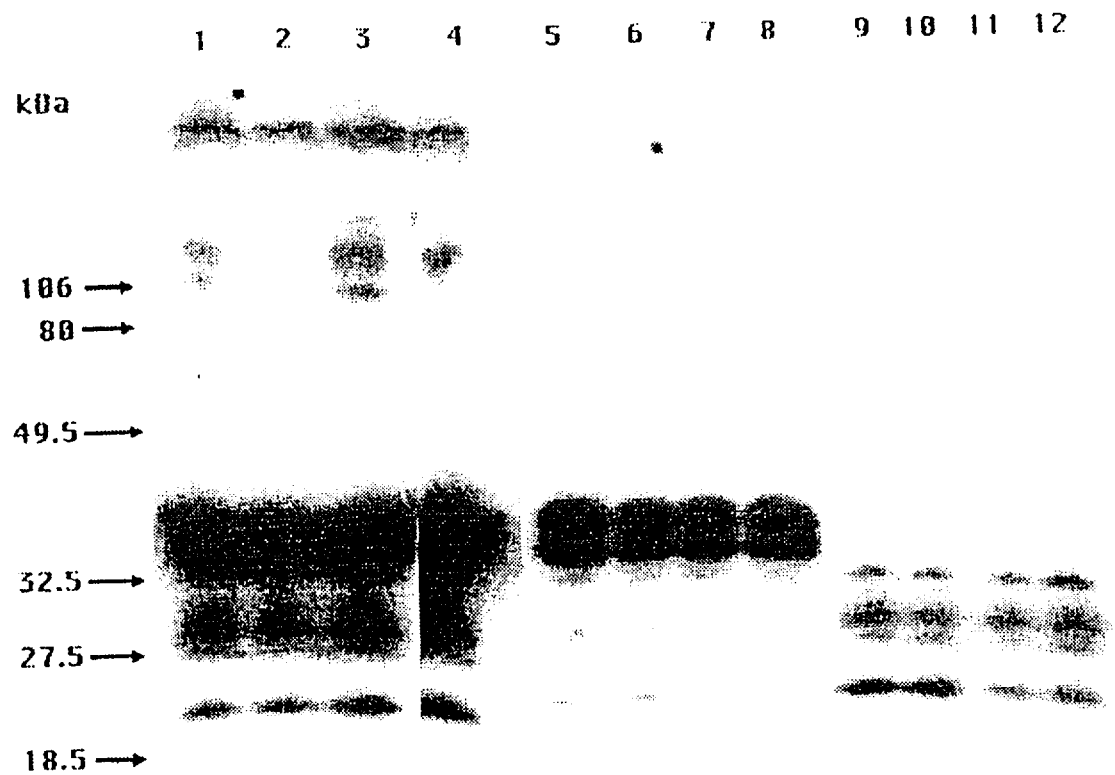
FIGS. 3A and 3B illustrate Western ligand blot analysis of IGF pools obtained following extraction by acid ethanol extraction, C18 SEP-PAK separation and SEPHADEX G-75 acid gel filtration.
Figure 3B:
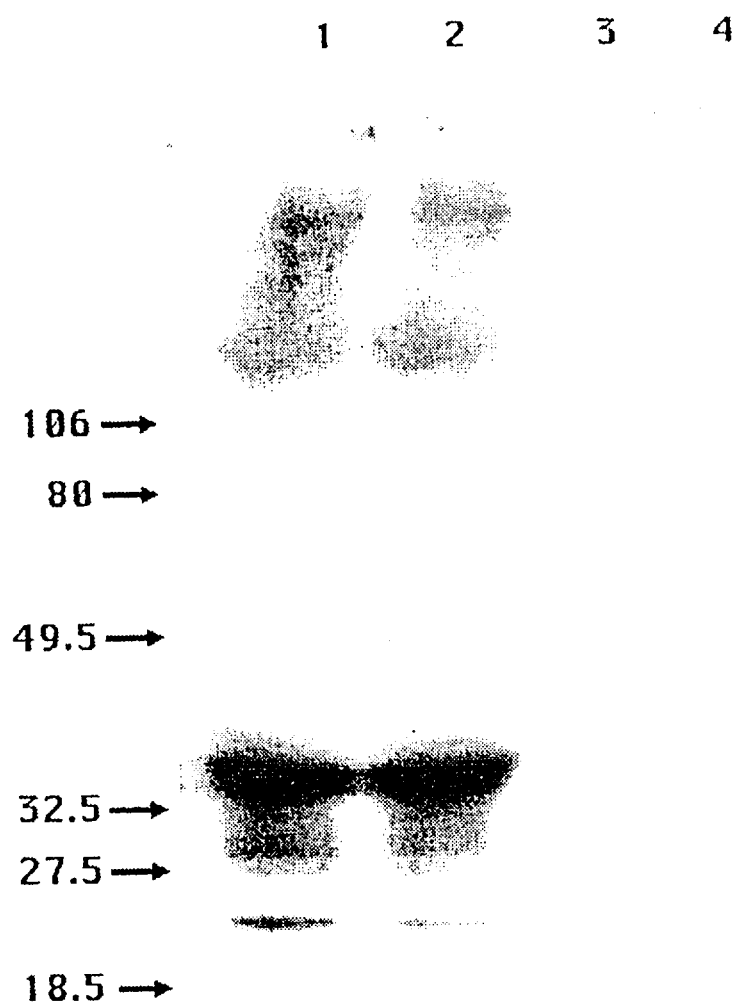

The results obtained with SEPHADEX G-75 separation of acid-ethanol and SEP-PAK separated IGF pools were further confirmed by a second method. Extracted serum samples were subjected to Western ligand blot analysis for quantification of IGFBPs (FIGS. 3A and 3B).

Samples were electrophoresed on 3–27% polyacrylamide gel in the presence of sodium dodecyl sulfate (SDS) under non-reducing conditions to separate different IGFBPs from each other and separate IGFS from IGFBPs. Prestained molecular weight markers (Bio-Rad, Richmond, Calif.) were run in each gel as standards. After electrophoresis, the gels were washed in T buffer (0.025M tris, 0.192M glycine, 20% methanol) for 15 minutes to remove SDS before electrotransfer onto nitrocellulose membrane (0.45 µm, Schleissher and Schuell Inc., Keene, N.H.) using T buffer. The proteins immobilized on nitrocellulose membrane were incubated with 2×10$^6$ cpm of $^{125}$I-IGF-I and $^{125}$I-IGF-II at 4° C., washed, and visualized by autoradiography according to the method of Hossenloop et al. *Anal. Biochem.*, 154:138 (1986).

Both acid-ethanol and SEP-PAK methods were found to be efficient in removing higher molecular weight proteins (presumably IGF receptors), but not low molecular weight IGFBPS. In contrast to acid-ethanol and SEP-PAK procedures, FPLC acid gel filtration using SEPHADEX G-75 resulted in complete removal of IGFBPs from serum as no IGFBP bands could be seen even following 2–3 weeks of exposure of nitrocellulose membrane to X-ray film at −70° C.

Example III

Separation of IGFs from IGFBPs by BIO-SPIN P-10 Chromatography

This example demonstrates separation of IGFs from IGFBPs by the methods of the present invention. Separation was both rapid and highly efficient.

BIO-GEL P-10 (45–90 µm particle size) was hydrated in excess 1M acetic acid containing 0.1M NaCl (in the absence or presence of 10 mg/ml BSA) overnight at room temperature. The gel was degassed for 10–15 minutes with occasional swirling of the flask. The gel solution was allowed to settle until 90–95% of the particles had settled. The supernatant containing fine particles was removed and the gel slurry was poured to empty BIO-SPIN columns (Bio-Rad, Hercules, Calif.) to a packed column bed height of 4 cm. The column was capped both at the bottom and top and stored at room temperature until use. Prior to use, the column was placed in a collection tube (10×17 mm polypropylene tube) and centrifuged for 3–5 minutes to remove the excess buffer in a swinging bucket at 3000 rpm (1250×g) in a Beckman Model T6J centrifuge (Beckman Instruments, Palo Alto, Calif.).

Fifty µl of sample (50 µl serum was mixed with 200 µl of 1.25M acetic acid with 0.125M NaCl and incubated for 30 minutes) was then carefully applied to the center of the column and centrifuged for 3–5 minutes. Fifty µl of elution buffer (1M acetic acid in 0.1M NaCl) was added and the column centrifuged again. More than 95% of IGFBP eluted during the first 2 centrifugations. The column was rinsed with 1 ml of elution buffer and centrifuged for 5 minutes to elute the IGFs. The eluant of each fraction was collected in a different collection tube (IGF pool) and dried by speed vac centrifugation. The IGF pool was reconstituted with 200 µl of 20 mM acetic acid and sonicated for 1 minute to dissolve the IGFs. The IGF fractions were further diluted with assay buffer, 50 mM phosphate buffer containing 0.25% BSA (pH 7.5), and used for IGF-I and IGF-II radioligand assays as described in Example I above.

Figure 4:
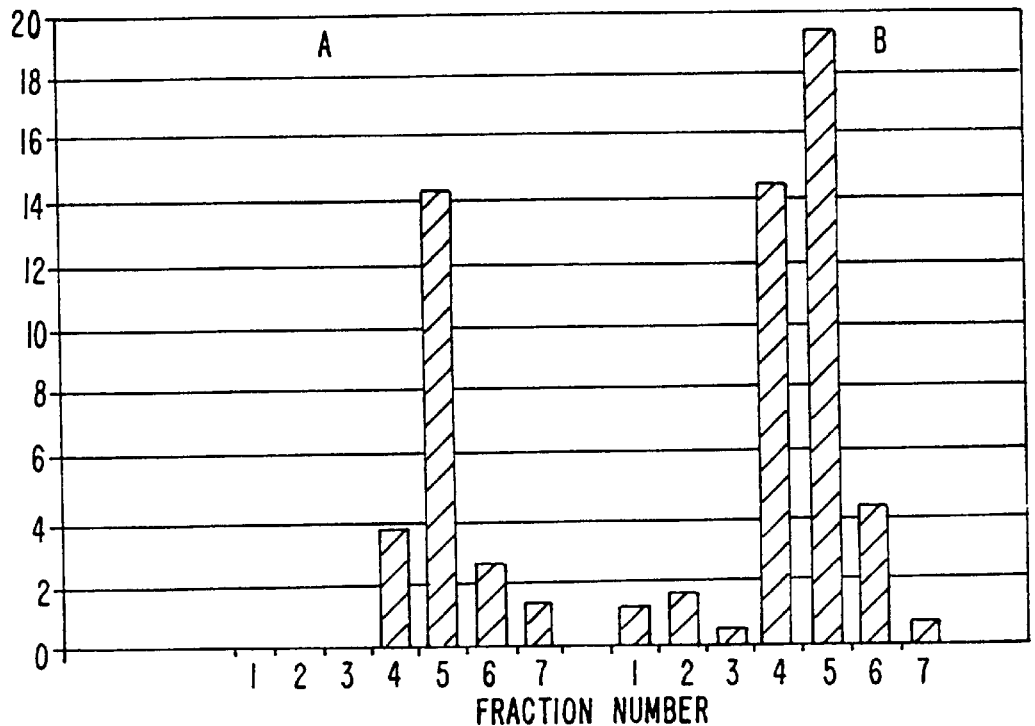
FIG. 4 illustrates the elution profile of labelled IGF-I in the presence and absence of normal human serum obtained using the methods of the present invention.
Figure 5:
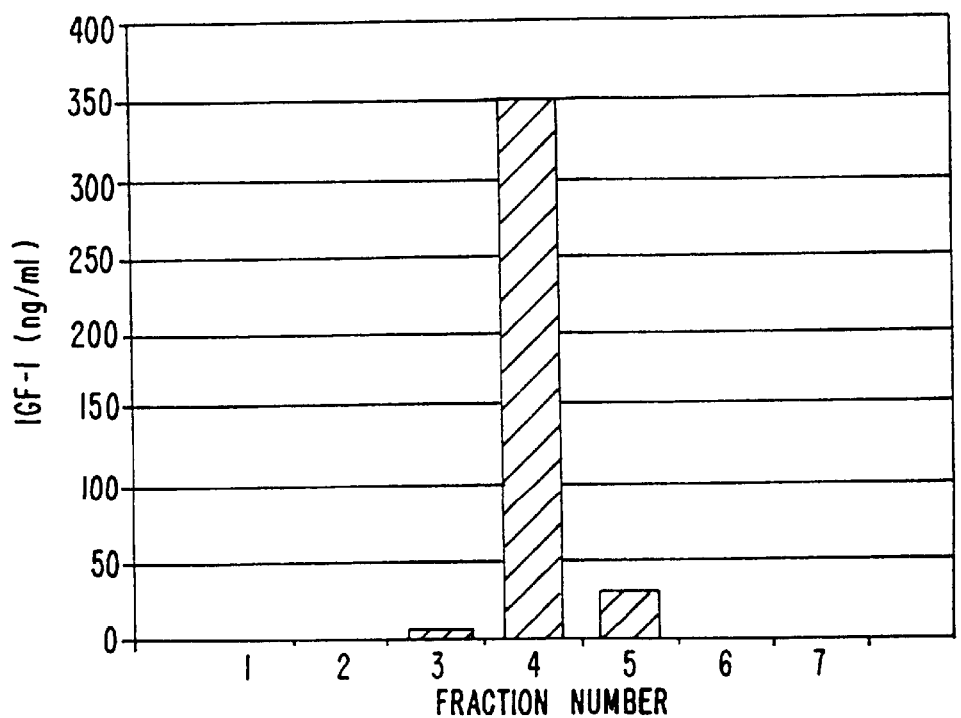
FIG. 5 demonstrates the elution profile of purified IGF-I using the methods of the present invention.

FIG. 4 illustrates the elution profile for $^{125}$I-IGF-I in the presence and absence of human serum using BIO-SPIN P-10 chromatography. The void volume fractions (1 & 2) contained less than 5% of total counts added. More than 95% of the total $^{125}$I-IGF-I recovered was found in fractions 4–6. FIG. 5 shows that when purified IGF-I was applied to BIO-SPIN P-10 column, no detectable IGF-I was found in column fractions 1 & 2 and that fractions 4 & 5 contained greater than 90% of the IGF-I recovered.

Figure 6A:
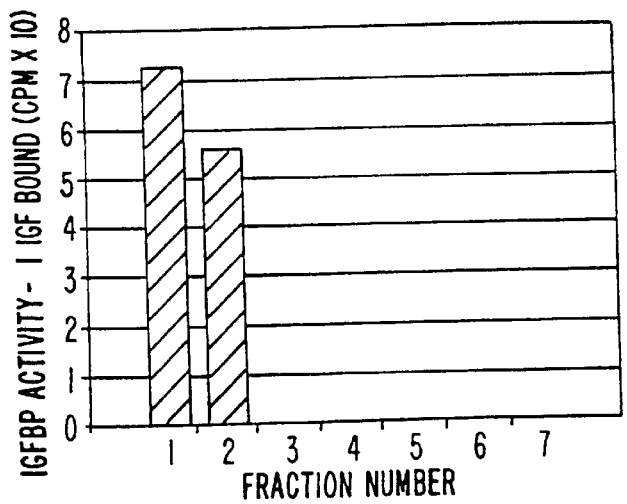
FIG. 6A illustrates the elution profile of IGFBPs using the methods of the present invention.
Figure 6B:
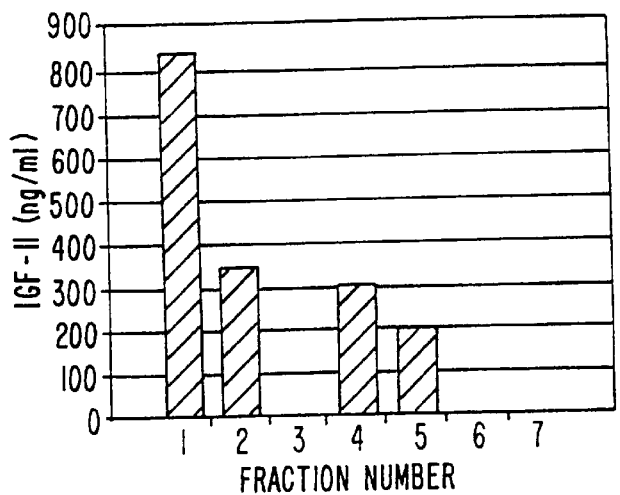
FIG. 6B illustrates the elution profile of IGF-I using the methods of the present invention.
Figure 6C:
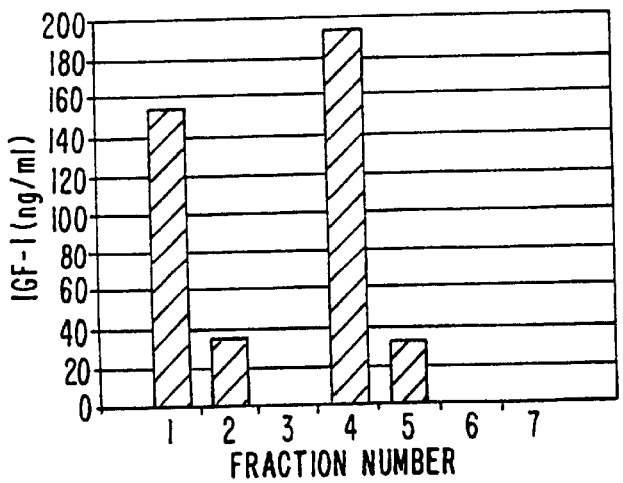
FIG. 6C illustrates the elution profile of IGF-II using the methods of the present invention.

FIGS. 6A–6C illustrate the profile for IGFBP, IGF-I, and IGF-II in BIO-SPIN P-10 column fractions when 50 µl of acidified serum (10 µl serum+40 µl 1.25M acetic acid containing 0.125M NaCl) was subjected to BIO-SPIN P-10 chromatography. IGFBP activity was determined by polyethylene glycol precipitation of $^{125}$I-IGF-I+IGFBP complex. Activity was found in fractions 1 & 2 with no detectable IGFBP activity in fractions 3–7 (FIG. 6A). In contrast to IGFBP activity, there were two peaks of IGF-I activity, peak 1 corresponding with the elution position of IGFBPs and peak 2 corresponding with the elution position of $^{125}$I-IGF-I. See FIG. 6B. Similarly, there were 2 peaks of IGF-II activity which corresponded with the elution positions of IGFBPs and $^{125}$I-IGF-II respectively. See FIG. 6C. IGF-I and IGF-II activity in peak 1 appeared to be due to IGFBP artifacts since this activity could be abolished upon preincubation of these fractions with excess of IGF-II or IGF-I prior to radioligand assays. The artifacts produced by IGFBPs appeared to be significantly higher in the IGF-II RIA than IGF-I RIA as the IGF-II-like activity in the IGFBP peak was 3–5 times higher than the actual IGF-II while the IGF-I like activity in IGFBP peak was 1–2 times higher than the actual IGF-I. The absence of any detectable IGFBP activity or IGF activity in fraction 3 suggested that the separation of IGFBPs and IGFs is complete with no overlap in the elution between IGFs and IGFBPs under the chromatographic conditions employed.

Similar experiments were performed employing BIO-GEL P-30 in place of BIO-GEL P-10. BIO-GEL P-30 has a nominal exclusion limit of 40 kDa. Separation with BIO-GEL P-30 was less efficient in separating IGFBPs from IGFs. Separation of IGFBPs and IGFs in normal human serum using BIO-GEL P-30 revealed that majority of IGFBPs eluted in fractions 1–3 compared to fraction 1 using BIO-GEL P-10 chromatography. In addition, IGFBPs were not completely separated from IGFs as fraction 3 contained both IGFBPs and IGFs. Thus, BIO-GEL P-30 chromatography was not as efficient as BIO-GEL P-10 for separating the IGFs from IGFBPs.

Example IV

Pretreatment of BIO-GEL P-10 with BSA

This example demonstrates the recovery of IGFs when separated from IGFBPS by the methods of the present invention on gels that had been pretreated with BSA and gels that had not been pretreated. Pretreatment with BSA increased the efficiency of IGF recovery.

Gel centrifugation columns were prepared for separation and extraction of IGFs. Ten grams of BIO-GEL P-10 soaked in 150 ml of 1M acetic acid containing 0.1M NaCl and allowed to hydrate for 30 minutes. 1.5 gms BSA was added and the BSA allowed to dissolve without shaking. After the BSA dissolved, the beads were gently mixed and incubated overnight. The gel was degassed and used to prepare BIO-SPIN columns 4 cm high.

Solutions of purified IGF-I were separated by pretreated and non-pretreated gels by methods as described in Example III. The recovery of purified IGF-I in the absence of serum after BIO-SPIN P-10 separation was low (less than 40%). In addition, the recovery of IGF-I was significantly increased if the serum samples were applied to BIO-SPIN columns that had been used previously for separation of IGFs from IGFBPs in serum. The results are demonstrated in Tables 1 and 2 below.

TABLE 1

IGF-I determination in human serum samples using BIO-SPIN P-10 columns

| | IGF-I (ng/ml) | | |
|---|---|---|---|
| Sample # | run-1 | run-2 | run-3 |
| 1 | 108 | 365 | 372 |
| 2 | 125 | 187 | 186 |
| 3 | 48 | 194 | 209 |
| 4 | 145 | 338 | 287 |
| 5 | 86 | 200 | 218 |
| 6 | 61 | 96 | 97 |
| 7 | 49 | 212 | 210 |
| 8 | 74 | 140 | 153 |
| Mean ± SD | 87 ± 36 | 217 ± 92 | 217 ± 83 |

100 μl human serum was mixed with 400 μl of 1.25M acetic acid containing 0.125M NaCl and 50 μl loaded to BIO-SPIN P-10 separation as described in the methods (run 1). The same columns were used for two more runs (runs 2 & 3). Values represent average of 2 replicate columns for each sample.

Table 1 shows that the recovery of IGF-I in 8 human serum samples after the first run was 40–50% of the subsequent runs. There was no significant difference between runs 2 and 3. A significant amount of IGFs were lost during the first run due to non-specific binding of IGFs to the BIO-GEL P-10 beads, even in the presence of 1M acetic acid. This non-specific binding of IGFs to beads could be substantially eliminated by pretreating the BIO-GEL P-10 beads overnight with serum proteins or BSA. Table 2, below, shows that >50% of $^{125}$I-IGF-I was retained in the column if BIO-GEL P-10 beads were soaked only in 1M acetic acid prior to use.

TABLE 2

Recovery of $^{125}$I-IGF-I using untreated, serum protein treated and BSA treated BIO-GEL P-10

| | Treatment of BIO-GEL P-10 beads | | |
|---|---|---|---|
| Fraction | None | Serum proteins | BSA |
| IGFBP pool | 0.6 ± 0.05 | 3 ± 0.8 | 2.5 ± 1.0 |
| IGF pool | 42.0 ± 2.8 | 92.0 ± 3.0 | 96.5 ± 5.0 |
| Column | 57.0 ± 3.6 | 1.3 ± 0.5 | 0.9 ± 0.2 |

BIO-GEL P-10 was soaked in 1M acetic acid containing 0.125M NaCl with no addition or with 1% human serum proteins or 1% BSA overnight to preparation of column. 50 μl of buffer containing $^{125}$I-IGF-I (100,000 cpm) was then added to each column prior to centrifugation as described in the methods. The values represent the percentage of $^{125}$I-IGF-I recovered in each fraction and are Mean ± SD of 4 replicate runs for each treatment.

As shown above, pretreatment of BIO-GEL P-10 beads with 1% serum proteins or 1% BSA significantly reduced non-specific binding (<2% of added $^{125}$I-IGF-I was retained in the column). Consistent with this data, mean IGF-I recovery in normal human serum pool using BSA pretreated and untreated BIO-GEL P-10 were 221±5 and 95±13 ng/ml (Mean±SD, n=5, P<0.001), respectively. In addition, it was found that there was no significant difference in the recovery of IGF-I after 1, 2, or 3 runs if BSA pretreated BIO-GEL P-10 was used for separation.

To determine the recovery of purified IGF-I after BIO-SPIN P-10 separation, 50 μl of 250 ng/ml IGF-I in 1M acetic acid, 0.1M NaCl was applied to the column. The amount of IGF-I in IGF pool was determined after BIO-SPIN separation. The amount of IGF-I recovered in 4 different samples was 91±2.5% (Mean±SD) of the added IGF-I. In addition, the recovery of exogenously added IGF-I to serum samples was determined by adding different concentrations of IGF-I prior to application to BIO-SPIN P-10 separation. The recovery of exogenously added IGF-I was greater than 90%.

In order to determine if the BIO-SPIN P-10 separation technique could be applied for separation of IGFs in conditioned media samples containing low levels of IGF-I, 1 ml DMEM containing 50 ng/ml IGFBP-3 and various concentrations of IGF-I (0.25 to 2 ng/ml) were dried by speed vac centrifugation, reconstituted in 100 μl of 1M acetic acid and applied to BIO-SPIN P-10 chromatography. Subsequent analysis of IGF-I in IGF pools revealed that the recovery of added IGF-I varied between 89% to 111% in different samples suggesting that BIO-SPIN P-10 separation could also be used for valid determination of IGFs in biological fluids containing low levels of IGFs, such as conditioned media samples.

Example V

Reproducibility of BIO-SPIN P-10 Chromatography

This example demonstrates the intra- and inter-assay reproducibility of IGF separation and measurement by the methods of the present invention. Each assay was performed as described in Example III above.

One serum sample was applied to 6 different columns and the recovery of IGF-I was determined after BIO-SPIN separation. The results are presented in Table 3 below.

TABLE 3

Separation of IGFs from IGFBPs - Intraassay variation

| Column | IGF-I (ng/ml) | NA |
|---|---|---|
| 1 | 240 | NA |
| 2 | 255 | NA |
| 3 | 267 | NA |
| 4 | 224 | NA |
| 5 | 240 | NA |
| 6 | 245 | Mean ± SD = 245 ± 15 (6% CV) |

100 μl normal human serum pool was diluted with 400 μl of 1.25M acetic acid containing 0.125M NaCl and 50 μl sample was applied to six BIO-GEL P-10 columns. IGF-I concentration was determined in the IGF pool by RIA as described in the methods.

Figure 7:
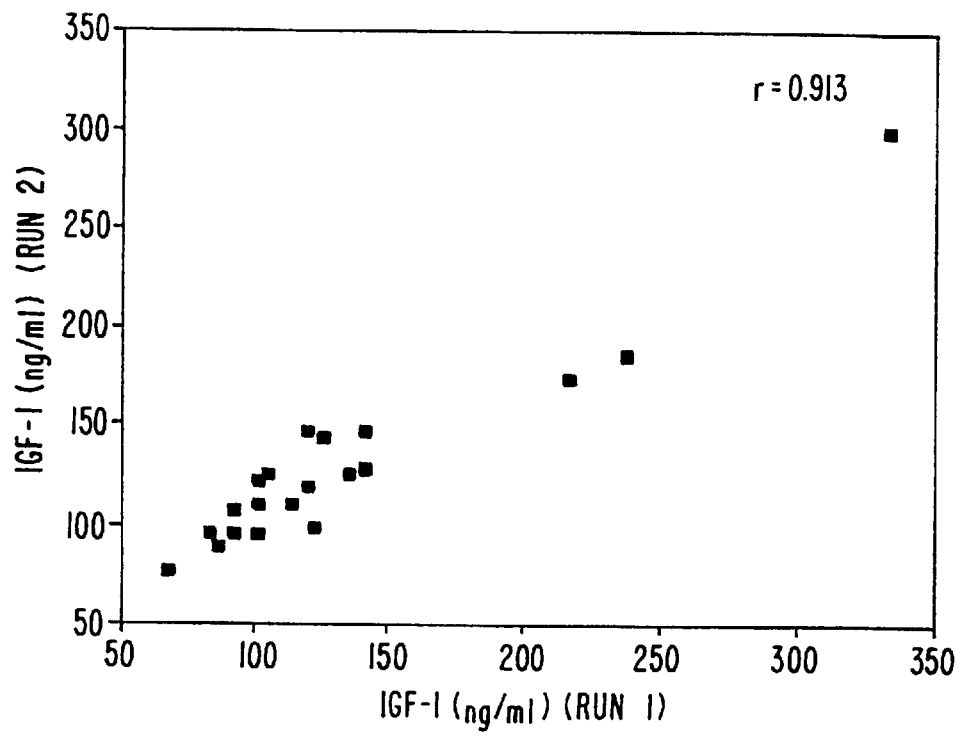
FIG. 7 illustrates interassay variability of the methods of the present invention.

The intraassay column variation for 6 columns was 6%. To determine interassay variation, 20 serum samples were subjected to BIO-SPIN P-10 chromatography on different days. FIG. 7 shows that the correlation coefficient for IGF values obtained for the 2 runs was 0.913 (P<0.001).

Example VI

Validation Of BIO-SPIN P-10 Chromatography

This example demonstrates the reliability of the methods of the present invention as compared to SEPHADEX G-75 acid gel filtration. Separation of IGFs and IGFBPs by the methods of the present invention correlated well with separation by SEPHADEX G-75 filtration.

Figure 8A:
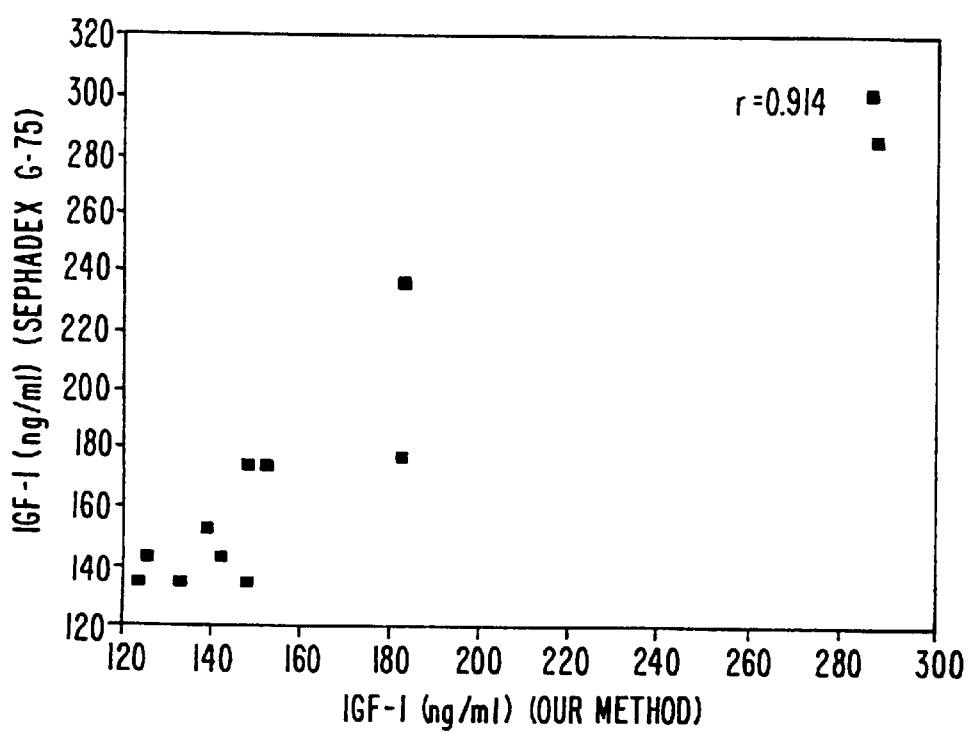
FIGS. 8A and 8B illustrate the correlation of IGF and IGFBP separation between SEPHADEX G-75 acid gel filtration, FPLC (fast protein liquid chromatography gel filtration and the methods of the present invention.
Figure 8B:
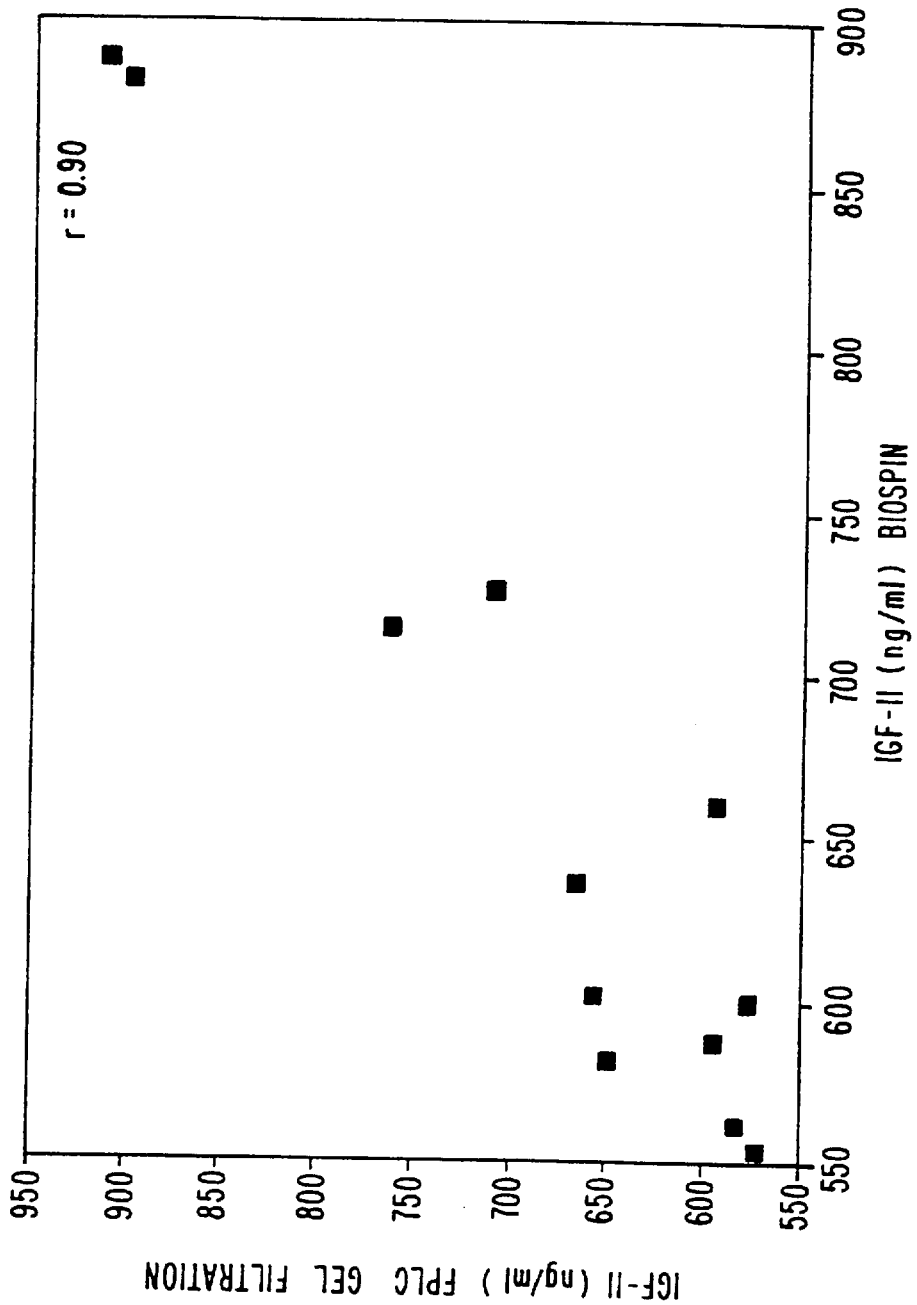

IGFs were separated from IGFBPs in ten normal human samples by SEPHADEX G-75 acid gel filtration in a FPLC and compared with the results obtained by BIO-SPIN separation. FIGS. 8A and 8B show the correlation between FPLC SEPHADEX G-75 separation and BIO-SPIN P-10 chromatography for IGF-I and IGF-II. Correlation between the methods was 0.914. In contrast to BIO-SPIN P-10 separation method, comparison of FPLC SEPHADEX G-75 versus acid-ethanol extraction or FPLC SEPHADEX G-75 versus SEP-PAK separation showed poor correlation for both IGF-I and IGF-II (Table 4).

TABLE 4

Correlation between FPLC SEPHADEX G-75 acid gel filtration, BIO-SPIN P-10 separation and acid ethanol extraction for removal of IGFBPs prior to IGF-I determination

| | r value | | |
|---|---|---|---|
| Method | FPLC | BIO-SPIN | Acid-ethanol |
| FPLC | 1.0 | 0.80 | 0.33 |
| BIO-SPIN | 0.8 | 1.0 | 0.44 |
| Acid-ethanol | 0.33 | 0.44 | 1.0 |

15 human serum samples were subjected to various pretreatments prior to IGF-I determination by RIA.

Figure 9:
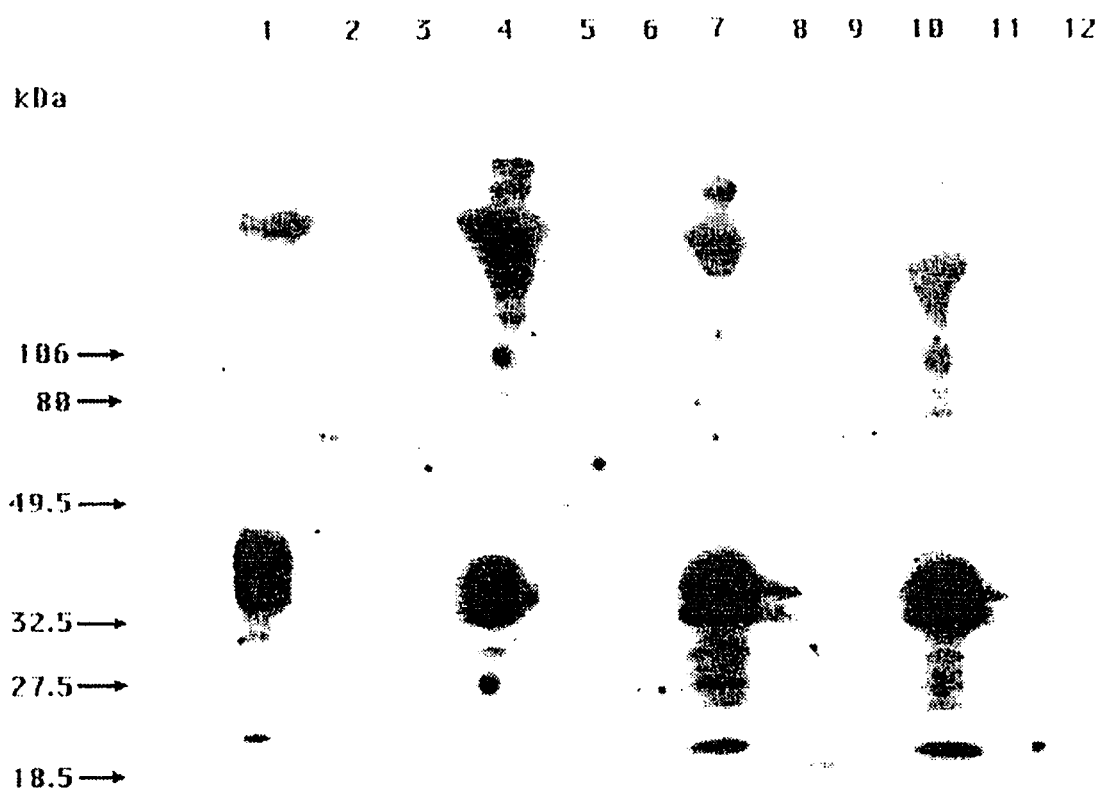
FIG. 9 illustrates a Western ligand blot analysis of fractions obtained following separation of IGFs from IGFBPs by the methods of the present invention.

The efficacy of the BIO-SPIN P-10 separation technique for removal of IGFBPs was further determined by using Western ligand blot analysis. An IGF pool obtained after BIO-SPIN P-10 separation contained no measurable IGFBP bands even after 3 weeks of exposure of nitrocellulose membrane to X-ray film (FIG. 9).

All publications, patents and patent applications mentioned in this specification are herein incorporated by reference into the specification to the same extent as if each individual publication, patent or patent application was specifically and individually indicated to be incorporated herein by reference.

Although the foregoing invention has been described in some detail by way of illustration and example for purposes of clarity of understanding, it will be obvious that certain changes and modifications may be practiced within the scope of the appended claims.

What is claimed is:

1. A method for separating an insulin-like growth factor (IGF) from its specific insulin-like growth factor binding protein (IGFBP) in a sample, comprising:
    acidifying the sample to dissociate the IGF from the IGFBP;
    applying the acidified sample to an acidic gel centrifugation column which comprises a gel which has been pretreated with a non-specific binding protein, wherein the column comprises a void volume;
    centrifuging the column to elute the IGFBP in the void volume;
    discarding the eluted IGFBP;
    applying an acidic buffer to the column and centrifuging to elute the IGF in one or more elution fractions; and
    collecting those eluted fractions that contain the IGF, thereby effecting a recovery of at least 89% of the IGF in the sample.

2. The method of claim 1, wherein the gel is resistant to a pressure of 5 psi.

3. The method of claim 2, wherein the gel is resistant to a pressure of 15 psi.

4. The method of claim 3, wherein the column is centrifuged at about 500–2000×g.

5. The method of claim 2, wherein the gel has a molecular size exclusion limit of between 8,000 daltons and 25,000 daltons.

6. The method of claim 5, wherein the gel has a molecular size exclusion limit of about 20,000 daltons.

7. The method of claim 1, wherein the gel has been hydrated with an acid.

8. The method of claim 7, wherein the acid is acetic acid or hydrochloric acid.

9. The method of claim 1, wherein the sample is blood, plasma, serum, urine, or conditioned medium.

10. The method of claim 1, wherein the non-specific protein is a human serum protein or bovine serum albumin.

11. The method of claim 1, wherein the non-specific protein is a serum protein.

12. A method of determining the concentration of insulin-like growth factor (IGF) in a sample, comprising:
    acidifying the sample to dissociate the IGF from any insulin-like growth factor binding protein (IGFBP) which may be present in the sample,
    applying the acidified sample to an acidic gel centrifugation column which comprises a gel which has been pretreated with a non-specific binding protein, wherein the column comprises a void volume;
    centrifuging the column to elute the contents of the void volume;
    discarding the eluted contents of the void volume;
    applying an acidic buffer to the column and centrifuging to elute the IGF in one or more elution fractions;
    collecting those eluted fractions that contain the IGF, thereby effecting a recovery of at least 89% of the IGF in the sample;
    quantifying the amount of the IGF in the collected fractions by an immunoassay using at least one antibody or by a receptor assay; and
    determining therefrom the concentration of the IGF in the sample.

13. The method of claim 12, wherein the amount of the IGF is quantified by the immunoassay.

14. The method of claim 13, wherein the immunoassay is a competitive binding assay.

15. The method of claim 12, wherein the amount of the IGF is quantified by the receptor assay, wherein said receptor assay is a competitive binding assay.

16. The method of claim 12, wherein the gel is resistant to a pressure of 12 psi and has a molecular size exclusion limit of about 20,000 daltons.

17. The method of claim 12, wherein the gel has been hydrated with acetic acid or hydrochloric acid.

18. The method of claim 12, wherein the sample is blood, plasma, serum, urine, or conditioned medium.

19. The method of claim 12, wherein the non-specific protein is a human serum protein or bovine serum albumin.

20. The method of claim 12, wherein the non-specific protein is a serum protein.

21. A method for determining a ratio of the concentration of free insulin-like growth factor (free IGF) to the concentration of total insulin-like growth factor (total IGF) in a sample, comprising:
    buffering a first portion of the sample in a neutral buffer;
    applying the buffered first portion to a neutral gel centrifugation column;
    centrifuging the neutral column to elute a first elution fraction of the first portion;

applying a neutral buffer to the neutral column and centrifuging to provide a second or more elution fractions;

collecting all of the eluted fractions that contain the free IGF;

quantifying the amount of the free IGF in the collected fractions by an immunoassay using at least one antibody or by a receptor assay;

determining therefrom the concentration of the free IGF in the sample;

acidifying a second portion of the sample to dissociate the IGF from any insulin-like growth factor binding protein (IGFBP) which may be present in the sample;

applying the acidified second portion of the sample to an acidic gel centrifugation column, which comprises a gel which has been pretreated with a non-specific binding protein, wherein the column comprises a void volume;

centrifuging the column to elute the contents of the void volume;

discarding the eluted contents of the void volume;

applying an acidic buffer to the column and centrifuging to elute the total IGF in one or more elution fractions;

collecting those fractions eluted from the second portion that contain the IGF, thereby effecting a recovery of at least 89% of the total IGF in the acidified second portion of the sample;

quantifying the amount of the total IGF in the collected fractions from the acidified second portion of the sample by an immunoassay using at least one antibody or by a receptor assay;

determining therefrom the concentration of the total IGF in the sample; and calculating the ratio of the concentration of the free IGF to the concentration of the total IGF in the sample.

22. The method of claim 21, wherein the non-specific protein is a human serum protein or bovine serum albumin.

23. The method of claim 21, wherein the non-specific protein is a serum protein.

* * * * *